US011857532B2

(12) United States Patent
Rotig et al.

(10) Patent No.: US 11,857,532 B2
(45) Date of Patent: Jan. 2, 2024

(54) TREATMENT AND PREDICTION OF THERAPEUTIC RESPONSES IN PATIENTS SUFFERING FROM FRIEDREICH ATAXIA

(71) Applicants: INSERM (Institut National de la Santé et de la Recherche Médicale), Paris (FR); Université de Paris, Paris (FR); Assistance Publique—Hôpitaux de Paris (APHP), Paris (FR); Fondation Imagine, Paris (FR)

(72) Inventors: Anne Agnès Rotig, Paris (FR); Arnold Munnich, Paris (FR); Floriane Petit, Paris (FR)

(73) Assignees: INSERM (INSTITUT NATIONAL DE LA SANTE ET DE LA RECHERCHE MEDICALE), Paris (FR); FONDATION IMAGINE, Paris (FR); ASSISTANCE PUBLIQUE-HÔPITAUX DE PARIS (APHP), Paris (FR)

(*) Notice: Subject to any disclaimer, the term of this patent is extended or adjusted under 35 U.S.C. 154(b) by 197 days.

(21) Appl. No.: 17/418,981

(22) PCT Filed: Dec. 27, 2019

(86) PCT No.: PCT/EP2019/087060
§ 371 (c)(1),
(2) Date: Jun. 28, 2021

(87) PCT Pub. No.: WO2020/136233
PCT Pub. Date: Jul. 2, 2020

(65) Prior Publication Data
US 2022/0105073 A1 Apr. 7, 2022

(30) Foreign Application Priority Data
Dec. 28, 2018 (EP) .................... 18306863

(51) Int. Cl.
A01N 43/04 (2006.01)
A61K 31/70 (2006.01)
A61K 31/357 (2006.01)
A61K 31/194 (2006.01)
A61K 31/7076 (2006.01)

(52) U.S. Cl.
CPC .......... *A61K 31/357* (2013.01); *A61K 31/194* (2013.01); *A61K 31/7076* (2013.01)

(58) Field of Classification Search
None
See application file for complete search history.

(56) References Cited

U.S. PATENT DOCUMENTS

2018/0110775 A1 4/2018 Deftereos et al.

FOREIGN PATENT DOCUMENTS

WO 2018/115012 A1 6/2018

OTHER PUBLICATIONS

Ba et al.; "Dihydroartemisinin Exerts its Anticancer Activity through Depleting Cellular Iron via Transferrin Receptor-1"; PLOS One, vol. 7, No. 8, Aug. 10, 2012, p. e42703.
Drecourt et al.; "Impaired Transferrin Receptor Palmitoylation and Recycling in Neurodegeneration with Brain Iron Accumulation"; American Journal of Human Genetics, vol. 102, No. 2, Feb. 1, 2018, pp. 266-277.
Arber et al.; "Review: Insights into molecular mechanisms of disease in neurodegeneration with brain iron accumulation: unifying theories: Mechanisms of neurodegerneration with brain iron accumulation"; Neuropathology and Applied Neurobiology, vol. 42, No. 3, Apr. 1, 2016, pp. 220-241.

*Primary Examiner* — Patrick T Lewis
(74) *Attorney, Agent, or Firm* — WCF IP

(57) ABSTRACT

Friedreich ataxia (FRDA) is caused by a GAA repeat expansion in FXN gene that encodes a mitochondrial protein, frataxin, involved in iron sulfur complex (ISC) assembly. Frataxin deficiency results in abnormal ISC containing proteins, namely respiratory chain complex I-III and aconitases and accumulation of iron in brain and heart of patients. Here, the inventors show that FRDA fibroblasts are unable to limit iron uptake inducing a massive cytosolic iron accumulation and to a lesser extent in mitochondria. The inventors also observed increased transferrin receptor (TfR1) steady state levels and membrane TfR1 accumulation that they ascribed to impaired post-translational modification by palmitoylation as well as delayed transferrin recycling. Finally, the inventors showed that artesunate, dichloroacetate and Coenzyme-A improved TfR1 palmitoylation and thus represent candidate molecules for the treatment of patients with Friedreich ataxia. Thus the present invention relates to methods of treating Friedreich ataxia (FRDA) as well as to methods of predicting whether a patient suffering from FRDA will achieve a therapeutic response.

12 Claims, 9 Drawing Sheets

Figures 1A, 1B:
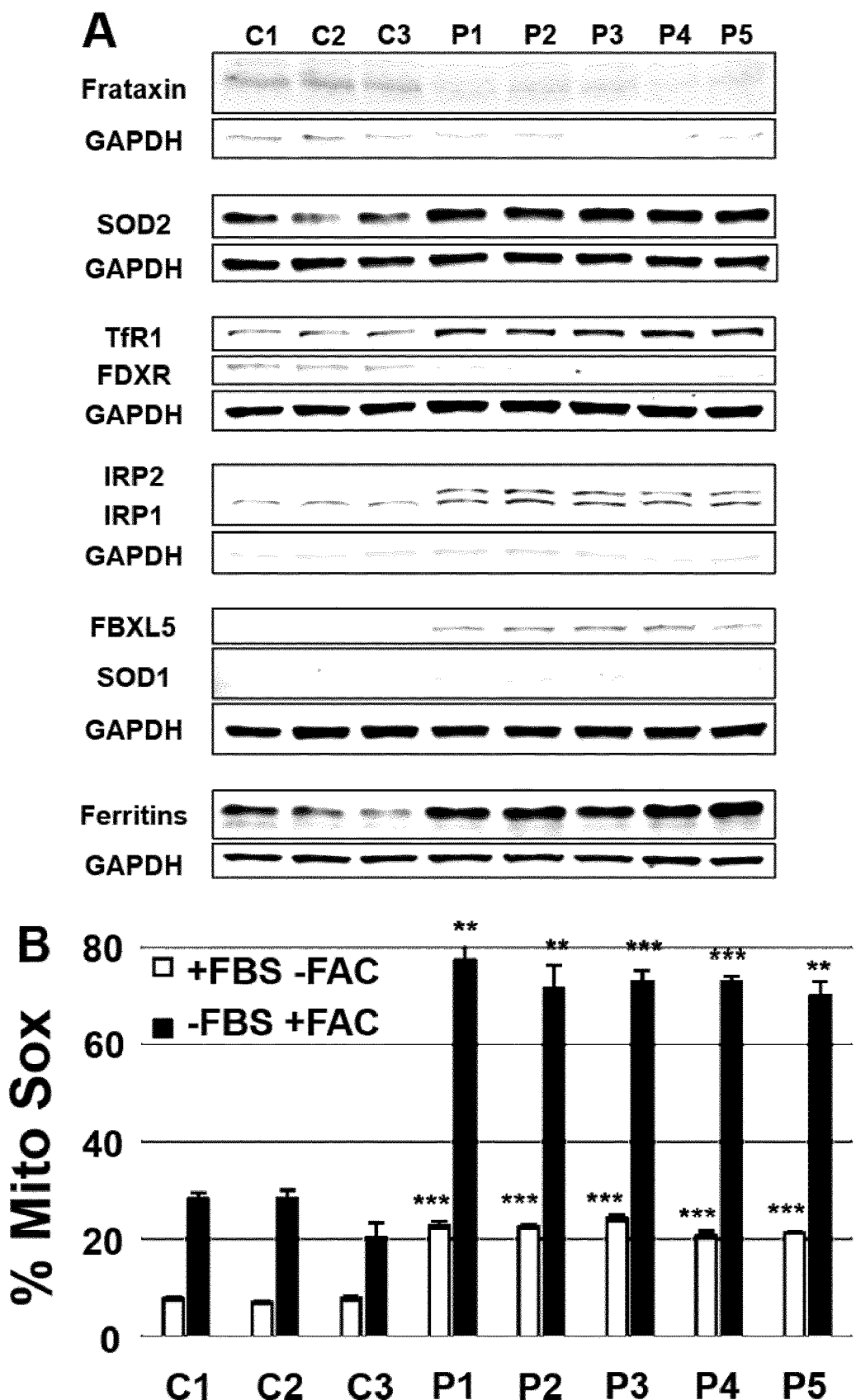

TREATMENT AND PREDICTION OF THERAPEUTIC RESPONSES IN PATIENTS SUFFERING FROM FRIEDREICH ATAXIA

FIELD OF THE INVENTION

The present invention relates to methods of treating Friedreich ataxia (FRDA) as well as to methods of predicting whether a patient suffering from FRDA will achieve a therapeutic response.

BACKGROUND OF THE INVENTION

Friedreich ataxia (FRDA) is a frequent autosomal recessive degenerative disease (1/50,000 live births) characterized by progressive gait and limb ataxia, lack of tendon reflexes in the legs, dysarthria and pyramidal weakness of the inferior limbs. A hypertrophic cardiomyopathy is observed in most FRDA patients. The disease causing gene, FXN, encodes a 210 amino acid mitochondrial protein, frataxin. FRDA is primarily caused by a GAA repeat expansion within the first intron of the frataxin gene that accounts for 98% of mutant alleles and results in decreased frataxin steady-state levels. Frataxin is involved in the first step of iron sulfur complex (ISC) assembly in which a [2Fe-2S] cluster is assembled on the Isu1 scaffold protein. This first step involves five other proteins including ferredoxin reductase that allows reduction of sulfur. Yet, the consequences of frataxin deficiency remain incompletely understood. Indeed, while mitochondrial respiratory chain deficiency has been ascribed to impaired complex I-III ISC assembly (Rotig et al., 1997), many other features remain unexplained, namely mitochondrial iron accumulation at the expense of cytosol with an increase of reactive oxygen species (ROS) (Vaubel and Isaya, 2013), deregulation of cellular iron metabolism (Martelli and Puccio, 2014), hyperacetylation of mitochondrial proteins mediated by SIRT3 inhibition (Wagner et al., 2012) and increased sphingolipids synthesis (Chen et al., 2016a). Recently, it was reported a novel mechanism of transferrin receptor (TfR1) regulation by palmitoylation and its alteration in neurodegeneration with brain iron accumulation (NBIA), a heterogeneous condition due to iron accumulation in basal ganglia (Drecourt et al., 2018). However, the existence of a similar mechanism in FRDA has never been investigated.

SUMMARY OF THE INVENTION

As defined by the claims, the present invention relates to methods of treating Friedreich ataxia (FRDA) as well as to methods of predicting whether a patient suffering from FRDA will achieve a therapeutic response.

DETAILED DESCRIPTION OF THE INVENTION

Friedreich ataxia (FRDA) is caused by a GAA repeat expansion in FXN gene that encodes a mitochondrial protein, frataxin, involved in iron sulfur complex (ISC) assembly. Frataxin deficiency results in abnormal ISC containing proteins, namely respiratory chain complex I-III and aconitases and accumulation of iron in brain and heart of patients. Here, the inventors show that FRDA fibroblasts are unable to limit iron uptake inducing a massive cytosolic iron accumulation and to a lesser extent in mitochondria. The inventors also observed increased transferrin receptor (TfR1) steady state levels and membrane TfR1 accumulation that they ascribed to impaired post-translational modification by palmitoylation as well as delayed transferrin recycling. Finally, the inventors showed that artesunate, dichloroacetate and Coenzyme-A improved TfR1 palmitoylation and thus represent candidate molecules for the treatment of patients with Friedreich ataxia.

Methods of Treatment:

Accordingly, the first object of the present invention relates to a method of treating Friedreich ataxia (FRDA) in a patient in need thereof comprising administering to the patient a therapeutically effective amount of an agent of a drug capable of increasing TfR1 palmitoylation.

As used herein, the term "Friedreich ataxia" or "FRDA" has its general meaning in the art and refers to a frequent autosomal recessive degenerative disease (1/50,000 live births) characterized by progressive gait and limb ataxia, lack of tendon reflexes in the legs, dysarthria and pyramidal weakness of the inferior limbs. A hypertrophic cardiomyopathy is observed in most FRDA patients. The disease causing gene, FXN, encodes a 210 amino acid mitochondrial protein, frataxin. FRDA is primarily caused by a GAA repeat expansion within the first intron of the frataxin gene that accounts for 98% of mutant alleles and results in decreased frataxin steady-state levels.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the drug is selected from the group consisting of artesunate, dichloroacetate and Coenzyme-A.

In some embodiments, the drug is artesunate. As used herein, the term "artesunate" has its general meaning in the art and refers to (3R,5aS,6R,8aS,9R,10S,12R,12aR)-Decahydro-3,6,9-trimetyl-3,12-epoxy-12H-pyrano[4,3-j]-1,2-benzodioxepin-10-ol, hydrogen succinate. The term encompasses any of the individual enantiorners of artesunate. In particular, the term may refer to just a single enantiomer, or a racemic or non-racemic mixture of the enantiomers. The term also includes polymorphs and hydrates of artesunate. The term also includes salts and esters of artesunate. The term also includes prodrugs of artesunate, and enantiomers, racemic mixtures, non-racemic mixtures, polymorphs, hydrates, salts and esters of said prodrugs.

As used herein, the term "dichloroacetate" has its general meaning in the art and refers to as the chemical compound with formula $CHCl_2COOH$. The term is also known as dichloroethanoic acid, bichloroacetic acid, DCA, BCA, dichloracetic acid, bichloracetic acid.

As used herein, the term "Coenzyme A" has its general meaning in the art and refers to a coenzyme, notably known for its role in the synthesis and oxidation of fatty acids, and the oxidation of pyruvate in the citric acid cycle. The IUPAC name is [[(2R,3S,4R,5R)-5-(6-aminopurin-9-yl)-4-hydroxy-3-phosphonooxyoxolan-2-yl]methoxy-hydroxyphosphoryl] [(3R)-3-hydroxy-2,2-dimethyl-4-oxo-4-[[3-oxo-3-(2-sulfanylethylamino)propyl]amino]butyl]hydrogen phosphate.

By a "therapeutically effective amount" of the drug as above described is meant a sufficient amount to provide a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the drug is administered to the subject in the form of a pharmaceutical composition. Typically, the drug may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The drug can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, or calcium, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

Methods for Predicting Therapeutic Responses:

A further object of the present invention relates to a method of determining whether a subject will achieve a response with a drug capable of increasing TfR1 palmitoylation comprising the steps of i) measuring the total cellular iron content of peripheral blood mononuclear cells (PBMCs) obtained from the subject cultured in a medium comprising an amount of iron, ii) comparing the iron content measured at step i) with a predetermined reference value and iii) concluding that the subject will achieve a response or not when differential between the content measure at step i) and the predetermined reference value is detected.

The method is thus particularly suitable for discriminating responder from non-responder. As used herein the term "responder" in the context of the present disclosure refers to a patient that will achieve a response. For instance, reduction of gait and/or limb ataxia, improvement of tendon reflexes in the legs, reduction in dysarthria and/or pyramidal weakness of the inferior limbs, as well as improvement of cardiac function represent hallmarks that the patient achieves a response. Typically, the characterization of the patient as a responder or non-responder can be performed by reference to a standard or a training set. The standard may be the profile of a patient who is known to be a responder or non-responder or alternatively may be a numerical value. Such predetermined standards may be provided in any suitable form, such as a printed list or diagram, computer software program, or other media. When it is concluded that the patient is a non-responder, the physician could take the decision to stop the therapy to avoid any further adverse sides effects.

The method of the present invention is particularly suitable for detecting earlier response of the patient in terms of reduction of total iron content of the cells. Measuring the total iron content represents therefore a surrogate marker for assessing the probability of success (i.e. response) with the treatment. Thus the method of the present invention is performed once the patient is treated with the drug (e.g. after 1, 2, 3, 4 or 5 cycles of treatment).

In some embodiments, the drug is selected from the group consisting of artesunate, dichloroacetate and Coenzyme-A.

As used herein, the term "PBMC" or "peripheral blood mononuclear cells" or "unfractionated PBMC", as used herein, refers to whole PBMC, i.e. to a population of white blood cells having a round nucleus, which has not been enriched for a given sub-population. Cord blood mononuclear cells are further included in this definition. Typically, the PBMC sample according to the invention has not been subjected to a selection step to contain only adherent PBMC (which consist essentially of >90% monocytes) or non-adherent PBMC (which contain T cells, B cells, natural killer (NK) cells, NK T cells and DC precursors). A PBMC sample according to the invention therefore contains lymphocytes (B cells, T cells, NK cells, NKT cells), monocytes, and precursors thereof. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis buffer which will preferentially lyse red blood cells.

Any culture medium suitable for growth, survival and differentiation of PBMC s may be used. Typically, it consists of a base medium containing nutrients (a source of carbon, aminoacids), a pH buffer and salts, which can be supplemented with serum of human or other origin and/or growth factors and/or antibiotics. Typically, the base medium can be RPMI 1640, DMEM, IMDM, X-VIVO or AIM-V medium, all of which are commercially available standard media.

Typically, the iron source in the culture medium is brought by ferric ammonium citrate (FAC). FAC is a soluble form of non-transferrin-bound iron (NTBI) that permeates into cells opportunistically via resident transporters or endocytic pathways.

In some embodiments, the total iron content is measured by any method known in the art. Typically the total iron content is measured using a ferrozine-based iron assay modified from (Barbeito et al., Mol Neurodegener. 2010 Nov. 10; 5:50.).

Typically, the PMBC are cultured for 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; or 50 h before measuring the total iron content, in particular the PMBC are cultured for 0, 8, 16, 24, 32, 40 h before measuring the total iron content.

In some embodiments, the predetermined reference value is a threshold value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the total iron content in a group of reference, one can use algorithmic analysis for the statistic treatment of the measured levels of the immune marker in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value is the total iron content of PBMC obtained from the patient before the treatment. In said embodiment, when the total iron content is lower (typically 0.5; 1; 2; 3; 4; 5; 6; 7; 8; 9; or 10 fold higher) than said predetermined reference value, it is concluded that the patient will achieve response with the drug. On the contrary when the total content iron is about the same as the predetermined reference value (or is higher than), it is concluded that the patient will not achieve a response with the drug.

In some embodiments, the predetermined reference value is the total iron content of PBMC obtained from the patient before the treatment and cultured in presence of the drug. In said embodiment, when the total iron content is higher (typically 0.5; 1; 2; 3; 4; 5; 6; 7; 8; 9; or 10 fold higher) than the predetermined reference value, it is concluded that the patient will not achieve response with the drug. On the contrary when the total content iron is about the same as the predetermined reference value (or is lower than), it is concluded that the patient will achieve a response with the drug.

The invention will be further illustrated by the following figures and examples. However, these examples and figures should not be interpreted in any way as limiting the scope of the present invention.

FIGURES

FIG. 1. Characterization of FRDA fibroblasts. A. Western blot analysis of frataxin and proteins involved in iron homeostasis and antioxidant defense in fibroblasts of five patients with GAA repeat expansions (P1-5) and controls (C1-3). Frataxin, ferritin, IRP1, IRP2, SOD1 and FBXL5 were studied in reducing condition and TfR1, SOD2 and ferredoxin reductase (FDXR) in non-reducing conditions (12% acrylamide, no dithiothreitol (DTT), no heat denaturation). GAPDH was used as a loading control. B. Measurement of mitochondrial reactive oxygen species (ROS) by flow cytometry using MitoSOX in control (C1-3) and FRDA fibroblasts (P1-5) in regular (+FBS, -FAC) or high iron medium (-FBS, +100 µM FAC). Data represent the percentage of MitoSox positive cells in controls and patients. C. Iron quantification using the ferrozine-based colorimetric assay in whole fibroblasts or mitochondrial extracts (D) of controls (C1-3) and FRDA patients (P1-5) grown in regular medium (+FBS, -FAC). E. Percentage of mitochondrial iron content relative to total cellular iron content. Unpaired sample t-test was used to compare patient's value to the mean of control value in B, C, D and E. *,  and * correspond to p values <0.5, <0.01 and <0.001 respectively.

FIG. 2. Regulation of iron homeostasis in FRDA fibroblasts. Post-transcriptional regulation of iron homeostasis of controls and FRDA fibroblasts grown in FBS-free DMEM medium in low (-FAC) or high iron conditions (+FAC). TfR1 (TFRC, A) and ferritin (FTH, B) mRNAs were quantified by ddPCR and expressed as a ratio to GUSB mRNA. The data are the means±SEM of three independent experiments. No significance of variations among samples and controls was estimated using 2-way ANOVA for multiple comparisons with Holm-Sidak method. Unpaired sample t-test was used to compare patient's value to the mean of control value. *,  and * correspond to p values <0.5, <0.01 and <0.001 respectively. C. Iron quantification using the ferrozine-based colorimetric assay in fibroblasts of controls (C1-3) and FRDA patients (P1-5) grown in FBS-free DMEM medium in low (-FAC) or high iron conditions (+FAC). Errors bars indicate SEM, n=3. Unpaired t-test was used to compare patient's value to the mean of control value.  and * correspond to p values <0.01 and <0.001 respectively, ns: non-significant. D. Steady-state levels of proteins involved in iron homeostasis. TfR1, SOD2 and FBXL5 were studied in non-reducing conditions (12% acrylamide, no dithiothreitol (DTT), no heat denaturation); ferritin and SOD2 in reducing conditions in controls (C1-3) and FRDA fibroblasts (P1-5) grown in FBS-free DMEM medium in low (-FAC) or high iron conditions (+FAC). GAPDH was used as loading control.

FIG. 3. TfR1 accumulation and defective Tf recycling in FRDA fibroblasts. A. Examples of TfR1 labeling in fibroblasts of control (C1 is representative of 3 controls) and FRDA fibroblasts (P1-5). Cell analysis was based on Hoechst positive signal. Scale bar, 10 µm. B. Quantification of membrane-bound TfR1 signal on at least 20,000 fibroblasts using the IDEAS software (Amnis Corporation). The data are the means±SEM of three independent experiments. Errors bars indicate SEM, n=3. Student's t-test was used to compare patient's value to the mean of control value.  and * correspond to p values <0.01 and <0.001 respectively. C. Relative mean fluorescence intensity of Tf-RED signal followed during 40 min in fibroblasts from controls (C1-3) and FRDA patients (P1-5) as a percentage of Tf-RED initial staining. The number of cells analyzed is higher than 20 in three independent experiments. The data are the means±SEM of three independent experiments. Holm-Sidak's multiple comparison test was used to compare patient's value to the mean of control value. *** corresponds to p value <0.001.

FIG. 4. TfR1 palmitoylation in FRDA fibroblasts. A. Fibroblasts from controls (C1-3) and FRDA patients (P1-5) were treated with DMSO alone (top left panel) or with 25 µM CoA for 72 h (top right panel), 5 mM dichloroacetate (DCA) for 72 h (bottom left panel), 25 µM artesunate for 48 h (bottom right panel), and TfR1 protein was immunoprecipitated with mouse anti-TfR1 antibody to perform the palmitoylation assay. In each condition, the upper panel shows the palmitoylated TfR1 level (IB: Biotin) and the immunoprecipitated amount of TfR1 (IB: TfR1). Input TfR1 is used as loading control for each condition. IP: immunoprecipitation, IB: immunoblotting. B. Iron quantification using the ferrozine-based colorimetric assay in fibroblasts of controls (C1-3) and FRDA patients (P1-5) grown in regular DMEM medium with or without 25 µM CoA for 72 h. Errors bars indicate SEM, n=3. 2-way ANOVA for multiple comparisons with Holm-Sidak multiple comparison test was used to compare patient's value to the mean of control value. *** corresponds to p values <0.001, ns: non-significant. C. Steady-state level of PDH-E2, lipoylated PDH-E2 (PDH-E2-LA) and lipoylated α-KGDH (α-KGDH-LA) in fibroblasts mitochondria from controls (C1-3) and FRDA patients (P1-5) untreated (−DCA) or treated with 5 mM DCA for 72 h (+DCA). Fibroblasts mitochondria were analyzed by immunoblot with antibodies against lipoic acid (that detects lipoic acid bound to PDH-E2 and α-KGDH). Porine was used as loading control.

Figure 5A:
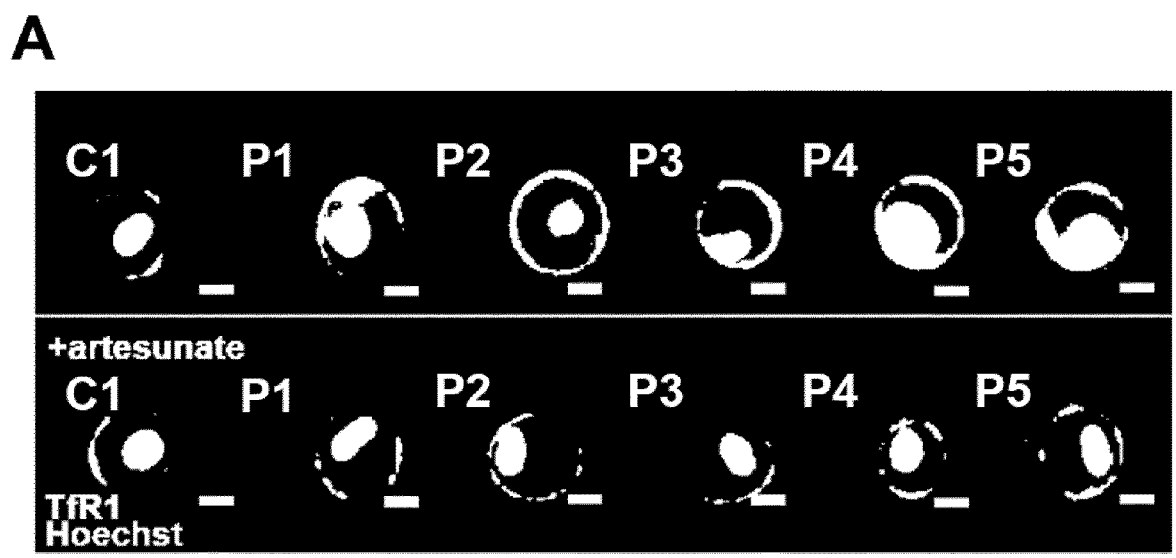

FIG. 5. Artesunate treatment reduces TfR1 accumulation and improve Tf recycling in FRDA fibroblasts. A. Examples of TfR1 labeling in fibroblasts of control (C1 is representative of 3 controls) and FRDA fibroblasts (P1-5) supplemented or not with 25 µM artesunate for 48 h. Cell analysis was based on Hoechst positive signal. Scale bar, 10 µm. B. Quantification of membrane-bound TfR1 signal on at least 20,000 fibroblasts of controls (C1-3) and FRDA patients (P1-5) using the IDEAS software (Amnis Corporation). Errors bars indicate SEM, n=3. C. Transferrin recycling. Relative mean fluorescence intensity of Tf-RED signal followed during 40 min in fibroblasts from controls (C1-3) and FRDA patients (P1-5) as a percentage of Tf-RED initial staining. The number of cells analyzed is higher than 20 in three independent experiments. The data are the means±SEM of three independent experiments. D. Iron quantification using the ferrozine-based colorimetric assay in fibroblasts grown in regular DMEM medium with or without 25 µM artesunate for 48 h. Errors bars indicate SEM, n=3. 2-way ANOVA with Holm-Sidak multiple comparison test was used in B, C and D. *,  and * correspond to p values <0.05, <0.01 and <0.001 respectively, ns: non-significant.

FIG. 6. Artesunate treatment improves iron homeostasis in FRDA fibroblasts. A. Iron quantification using the ferrozine-based colorimetric assay in fibroblasts grown in high iron condition (100 µM FAC) with or without 25 µM artesunate for 48 h. Errors bars indicate SEM, n=3. 2-way ANOVA with Holm-Sidak multiple comparison test was used. *** corresponds to p<0.001. B. Steady-state levels of proteins involved in iron homeostasis. TfR1, SOD2 and FBXL5 were studied in non-reducing conditions (12% acrylamide, no dithiothreitol (DTT), no heat denaturation) and IRP1, IRP2 and ferritin in reducing conditions in controls (C1-3) and FRDA fibroblasts (P1-5) grown in regular DMEM medium with or without 25 µM artesunate for 48 h.

FIG. 7. Iron content in FRDA PBMC. A. Measurement of iron content in PBMC grown in high iron medium (100 µM FAC). Iron content was measured each 8 h during 40 h using the ferrozine-based colorimetric assay in controls (C4-7), heterozygous carriers (carrier 1-3) of FXN GAA expansion and FRDA PBMC (P1, P6-14). B. Iron content in PBMC grown for 40 h in high iron medium (100 µM FAC) with or without 25 µM. C8-9 are controls, carriers 4-5 are heterozygous carriers of FXN GAA expansion and P15-16 are FRDA patients with compound heterozygous FXN GAA expansion.

EXAMPLE

Methods:

Informed consent for diagnostic and research studies was obtained for all subjects in accordance with the Declaration of Helsinki protocols and approved by local Institutional Review Boards in Paris.

Patients

Patients carried GAA repeat expansions in the first intron of the frataxin gene.

| | |
|---|---|
| P1 | 2.1 and 2.1 kb |
| P2 | 3.0 and 3.6 kb |
| P3 | 2.1 and 2.7 kb |
| P4 | 2.4 and 2.4 kb |
| P5 | |
| P6 | 2.1 and 2.4 kb |
| P7 | 2.2 and 2.8 kb |
| P8 | 2.4 and 2.7 kb |
| P9 | 1.5 and 2.4 kb |
| P10 | 2.5 and 3.0 kb |
| P11 | 1.7 and 1.9 kb |
| P12 | 2.8 and 2.8 kb |
| P13 | 2.9 and 3.4 kb |
| P14 | 2.5 and 2.5 kb |
| P15 | 2.6 and 2.6 kb |
| P16 | 2.5 and 2.5 kb |

Cell Culture

Skin fibroblasts were grown in Dulbecco's Modified Eagle Medium (DMEM, Life technologies) medium supplemented with 10% fetal bovine serum (FBS), 2 mM L-glutamine, 2.5 mM pyruvate, 100 µg/ml streptomycin, 100 U/ml penicillin at 37° C. For treatment with ferric ammonium citrate (FAC), 80% confluent cells were incubated for 72 h with or without 100 µM FAC in serum-free DMEM (i.e. Tf free). For drug treatment, 80% confluent cells were incubated in DMEM+10% FBS supplemented with 25 µM artesunate (Sigma) in DMSO for 48 h, 25 µM CoA (Sigma) for 72 h and 5 mM DCA (Sigma) for 72 h.

PBMC Isolation and Culture

PBMC were isolated from 8 ml blood samples by density centrifugation using Ficoll (GE Healthcare) and grown 2 h in regular DMEM before treatment with 100 µM FAC for different time.

Western Blot

Cultured skin fibroblasts were harvested on ice by scraping in reducing (2 µM dithiothreitol, DTT, denaturation at 95° C. for 5 min) or non-reducing cell lysis buffer (no DTT, no heat denaturation). Western bot analysis was performed on 20 µg of whole-cell protein extracts or mitochondrial-enriched fractions in 12% acrylamide gel or 4-15% gel gradient. Immunodetections were performed in PBS with 5% or 1% milk, 0.05% Tween20 (SIGMA) using the following antibodies: rabbit anti-SOD1 (Abcam, ab16831), rabbit anti-SOD2 (Abcam, ab13533), mouse anti-TfR1 (Invitrogen, 13-6800), rabbit anti-TfR1 (Abcam, 108985), rabbit anti-ferritin (Abcam, ab75973), rabbit anti-IRP1 (Abcam, ab126595), rabbit anti-IRP2 (Abcam, ab80339), rabbit anti-FBXL5 (Abcam, ab140175), rabbit anti-FDXR (Abcam, 204310), rabbit anti-FXN (Protein tech, 14147-1-AP), rabbit anti-PDH E2 subunit (Abcam, ab172617), rabbit anti-lipoic acid (Abcam, ab58724), goat anti-Biotin (Thermo, 31852), mouse anti-VDAC/Porine (Abcam, ab14734)

mouse anti-ATP5a (Abcam, ab14748), mouse anti-Vinculin (abeam, ab130007), rabbit anti-TFAM (Proteintech, 19998-1-AP), rabbit ATP8 (Proteintech, 26723-1-AP) and mouse anti-GAPDH antibodies (ab8245). Blots were incubated with fluorescent secondary antibodies (IRDye 800CW/680LT Goat anti-rabbit or anti-mouse IgG (LI-COR)) or HRP-conjugated secondary antibodies (goat anti-rabbit IgG HRP (Abcam), goat anti-mouse IgG HRP (Abcam) or donkey anti-goat IgG HRP (Santa Cruz)) before ECL-based detection (SuperSignal West Dura, Thermo Scientific). Signals captured either with the Odyssey Infrared Imaging System using Image Studio Lite v5.2 (LI-COR Biosciences) or with CDD camera using Image Lab v3.0 (BioRad).

MitoSOX

Mitochondrial superoxide was quantified by flow cytometry assay adapted from (Mukhopadhyay et al., 2007). Fibroblasts were supplemented with 10 µM MitoSox Red for 20 min, trypsinized and neutralized with fresh media (regular media or DMEM with FAC). Flow cytometry was carried out using Gallios (Beckman Coulter). MitoSOX Red was excited at 488 nm. Data were collected at FSC, SSC, 580 nm (FL2) channel in Kaluza software (Beckman Coulter) on at least 20,000 cells. Cell debris were gated out for analysis. Histograms of mean intensity of MitoSOX fluorescence were represented in FL2 channel.

Quantification of TFRC and FTH Transcripts

Total RNA was extracted using the RNeasy Mini Kit (Qiagen) and DNase treated by the RNase-free DNase set (Qiagen) according to manufacturer's protocol. Concentration and purity of total RNA was assessed using the Nanodrop-8000 spectrophotometer (Thermo) before storage at −80° C. Then mRNAs were reverse transcribed from 2 µg of total RNA using High-Capacity RNA-to-cDNA Kit (Thermo) according to the manufacturer's instructions using random priming. Quantitative RT-PCR (qRT-PCR) was performed with digital droplet PCR (ddPCR) using QX200 DropletDigital PCR System (Bio-Rad). TFRC and FTH cDNAs were amplified using specific primers. 0-glucuronidase (GUSB, NM_000181.3) was used for normalization. Data were analyzed on QX200 Droplet Reader using Quantasoft analysis software (Bio-Rad). TFRC and FTH expression levels were normalized to the mean copy numbers of GUSB housekeeping gene.

Iron Content and Imaging Flow Cytometry (Imagestream)

Fibroblasts were starved for one hour in FBS-free DMEM medium (i.e. Tf-free), treated with 5 mM EDTA for harvesting them without disrupting TfR1 located at cell surface, as trypsin does, and then labelled with anti-TfR1 antibody at 4° C. to avoid TfR1 internalization. In this condition only membrane-bound TfR1 is quantified. Cell sorting was based on Hoechst-positive signal, allowing to select living cells.

Total iron contents were measured using a ferrozine-based iron assay modified from (Barbeito et al., 2010). For imaging flow cytometry, fibroblasts were starved for one hour in FBS-free DMEM medium, treated with 5 mM EDTA for harvesting them without disrupting TfR1 located at cell surface, as trypsin does, washed 3 times with cold PBS and then labelled with anti-TfR1 antibodies (A24) (Moura et al., 2004) for 1 h on ice to avoid TfR1 internalization. In this condition, only membrane-bound TfR1 is quantified. Secondary staining was performed using Alexa fluor 488 goat anti-mouse antibody (Life technology) for 30 min on ice. Cells were washed and stained with Hoechst for 5 min in a total volume of 50 µl and acquisitions were directly performed. Cell analysis was based on Hoechst-positive signal, allowing to select living cells. Samples were run on an Imagestream ISX mkII (Amnis Corp, Millipore, Seattle, WA) that combines flow cytometry with detailed cell-imaging and functional studies and a 40× magnification was used for all acquisitions. Data were acquired using the INSPIRE software (Amnis Corp) and analyzed using the IDEAS™ software (version 6.2 Amnis Corp) on at least 20,000 events. Spectral compensation was performed using singly stained samples. A specific mask was designed for analysis of the membrane localization of TfR1. This mask was the result of a full bright field mask minus a 5 pixels erode and 1 pixel dilate bright mask resulting in doughnuts-like mask. Results were expressed as mean pixel intensity value which is the intensity normalized to surface area.

Confocal Microscopy

For Tf recycling, fibroblasts were spread at 30% confluence onto micro-slides glass bottom (IBIDI) 24 h before experiment. Cells were then starved in FBS-free DMEM media for 1 h before add Tf-RED (12.5 µg/mL) for 30 min at 37° C. Cells were washed with PBS and then incubated for in regular media for live-imaging acquisition using spinning disk confocal microscopy (ZEISS Microscopy). Slides were placed un incubation chamber at 37° C. under 5% $CO_2$. At least 20 cells were acquired by condition using 63× oil immersion objective lens with a picture of cell/min during 40 min using Zen software. The nuclear region (NR) was defined using Icy software v1.9. Each NR was enlarged two times to generate the perinuclear region of interest (PNROI). PNROI masks were then applied on RED channel by spot detector plugin to obtain quantitative mean fluorescence particle intensity. Only particles of at least 8 pixels size were considered. The mean intensity value was normalized to surface area. Data were expressed in percentage of Tf initial signal at time 0 min.

Palmitoylation Assay

TfR1 palmitoylation in cultured skin fibroblasts was modified from (Ba et al., 2012). Briefly, cells were lysed on ice in a DTT-free cell lysis buffer and endogenous TfR1 was immunoprecipitated overnight with mouse anti-TfR1 antibody (Life Technologies, 136890) with protein G magnetic beads (BioRad). After washing with PBS, beads were successively incubated 2 h with 50 mM N-ethylmaleimide (NEM) at room temperature, 1 M hydroxylamine and 50 mM HPDP-Biotin (Thermo) in dark for 2 hours. Samples were run in 12% acrylamide gel and biotin-labeled TfR1 level was determined by immunoblotting in non-reducing conditions using Chemidoc technology thanks to a CCD camera (BioRad) and ImageLab software v3.0 (BioRad).

Mitochondria Isolation

Mitochondria were isolated as described in (Metodiev et al., 2009) in Mito-isolation buffer (320 mM sucrose, 10 mM Tris-HCl pH 7.5 with Protease inhibitor cocktail in EDTA) by differential centrifugation. Mitochondria were resuspended in Mito-isolation buffer for protein analysis or conserved in dry-pellet for iron quantification.

Statistics

All statistical analyses were performed with GraphPad Prism 5.0 (GraphPad Software) using a two-tailed, unpaired ttest or 1-way ANOVA for multiple comparisons with Holm-Sidak method. *,  and * correspond to P values <0.05, <0.01 and <0.001 respectively, ns: non-significant.

Results

Characterization of Frataxin, TfR1 and IRPs in FRDA Fibroblasts

Frataxin steady-state levels were reduced to 30-68% of control values in cultured skin fibroblasts of FRDA patients (GAA repeat expansions >2.1 kb, FIG. 1A). Ferredoxin reductase (FDXR) steady-state level was also decreased, suggesting a co-regulation of the two proteins in FRDA fibroblasts (FIG. 1A).

Figures 1C, 1D, 1E:
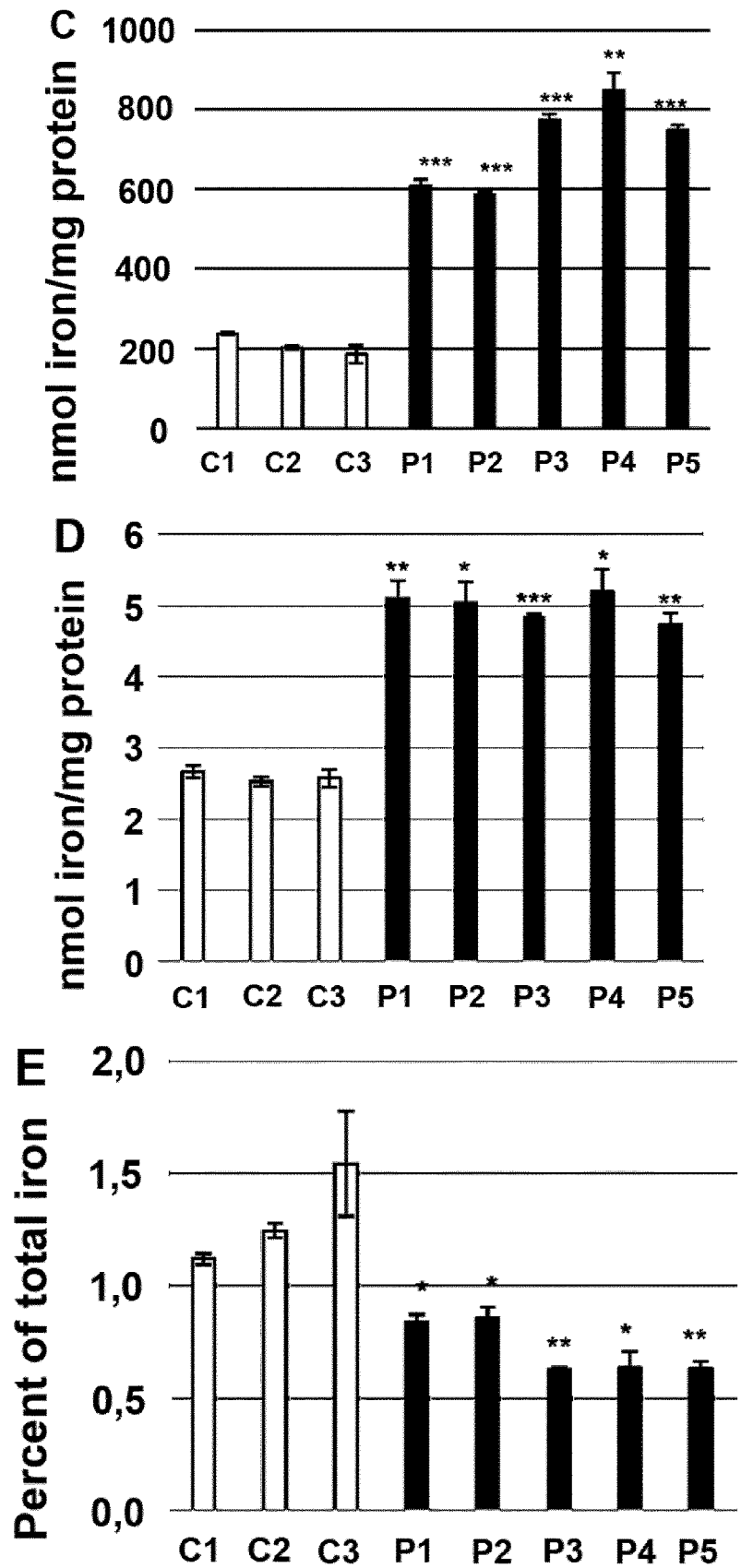

Cellular iron is mainly imported by transferrin-bound iron uptake by TfR1-mediated endocytosis. Homeostasis of cellular iron is regulated by a post-transcriptional mechanism involving iron regulatory proteins 1-2 (IRP1-2). IRPs regulate several iron-related genes at the post-transcriptional level, especially TfR1 and ferritin. Western blot analysis of FRDA fibroblasts showed increased steady-state levels of TfR1 (1.6 fold increase), IRP1 and IRP2 (2.2 and 2.4 fold increase respectively, FIG. 1A), mimicking iron starvation as previously reported following disruption of the mitochondrial ISC machinery (Muhlenhoff et al., 2015). Paradoxically, ferritin steady-state levels were also increased in FRDA fibroblasts (2.1 fold) which is inconsistent with elevated TfR1 and IRP1-2 and suggestive of cytosolic iron overload. F-box and leucine-rich repeat protein 5 (FBXL5), an iron sensor protein reflecting the labile iron pool was increased as well, also supporting cytosolic iron overload. Consistently, cytosolic superoxide dismutase SOD1 was increased (232% mean increase), suggesting a cytosolic stress possibly related to cytosolic iron overload (FIG. 1C). Mitochondrial superoxide dismutase SOD2 showed a two-fold increase, reflecting a severe oxidative stress possibly triggered by mitochondrial iron overload in FRDA fibroblasts (FIG. 1A). Consistently, a 2.5-fold increase of mitochondrial ROS was detected by flow cytometry using Mito-SOX in FRDA fibroblasts (FIG. 1B).

FRDA Fibroblasts Failed to Regulate Iron Uptake

Elevated ferritin and FBXL5 steady-state levels prompted to assess iron content in FRDA fibroblasts using a ferrozine-based iron assay modified from (Barbeito et al., 2010). In basal conditions, total cellular iron was 3-4-fold higher in FRDA fibroblasts compared to controls (FIG. 1C) while iron content in mitochondrial extracts was only two fold higher in FRDA compared to controls (FIG. 1D). Mitochondrial iron accounted for largely 1-1.5% of total iron in controls but only 0.6-0.8% in FRDA fibroblasts (FIG. 1E). Hence, FRDA fibroblasts mainly accumulate iron in the cytosol and to a lesser extent in mitochondria, suggesting that total cellular iron does not reflect the actual mitochondrial iron pool in FRDA fibroblasts.

Figures 2A, 2B, 2C:
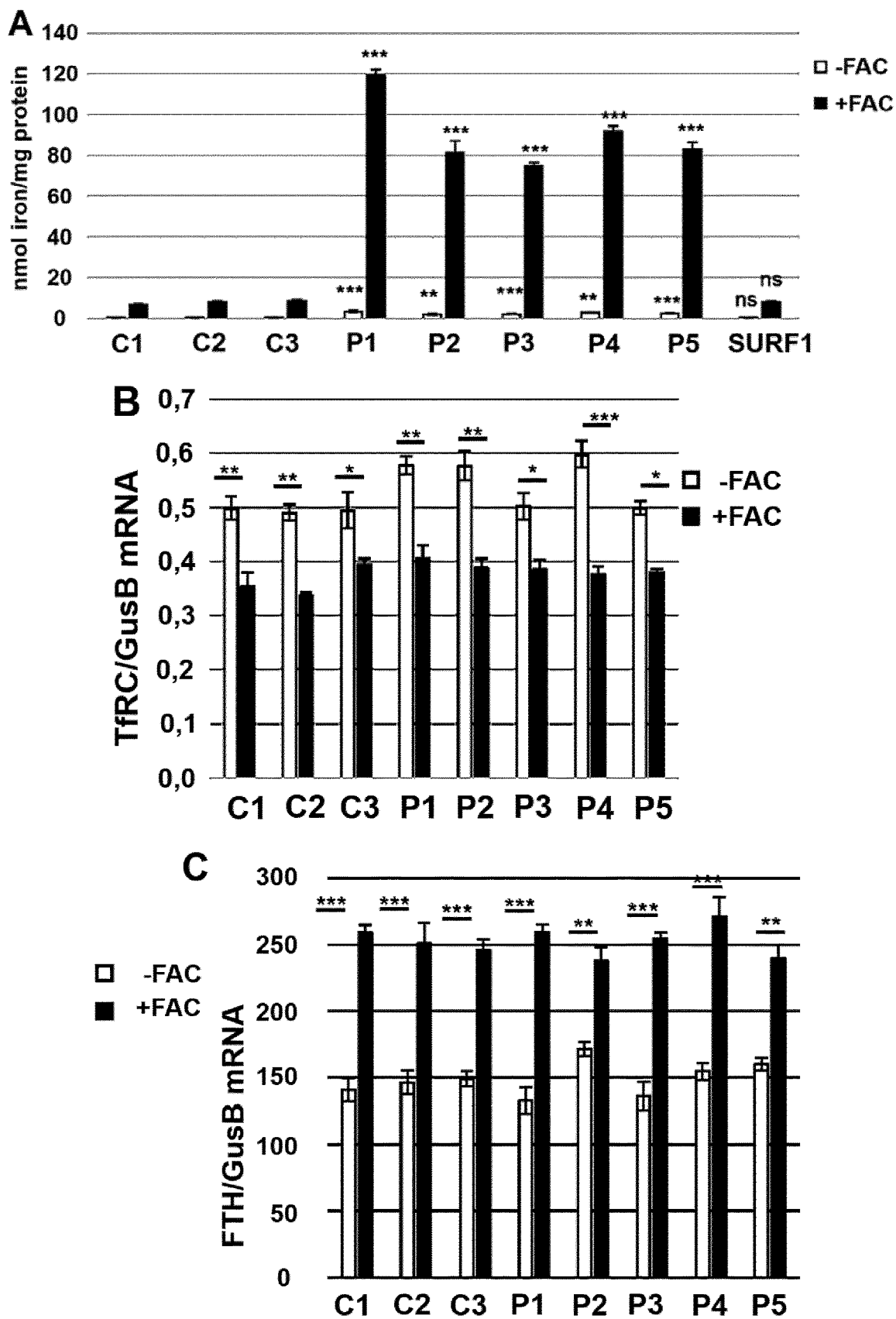

Cellular iron was quantified in either low (no fetal bovine serum, FBS, i.e. devoid of Tf-bound iron) or high iron conditions, brought about by ferric ammonium citrate (FAC). FAC is a soluble form of non-transferrin-bound iron (NTBI) that permeates into cells opportunistically via resident transporters or endocytic pathways. In low iron conditions (neither FAC, nor FBS), FRDA fibroblasts displayed a 2-4 fold higher iron content compared to controls (FIG. 2A). However, after a 3-day incubation with FAC, FRDA fibroblasts exhibited a major cellular iron increase (32-42 fold change) while control fibroblasts displayed a 10-fold increase (FIG. 2A). This was not due to respiratory chain deficiency as cellular iron levels in a patient carrying biallelic SURF1 mutations were similar to controls grown in the same conditions (FIG. 2A). These data suggested that cultured FRDA fibroblasts failed to regulate iron uptake and display a major iron overload when grown in high iron condition.

IRPs are sensor of cellular iron content. When cytosolic iron increases, IRP1 is converted into aconitase, while IRP2 is targeted to ubiquitination and proteasome degradation by the iron-binding protein, FBXL5. Decreased IRP1-2 down-regulates TfR1 and limits iron uptake while ferritin is up-regulated allowing cytosolic iron storage. Considering the major iron overload of FRDA fibroblasts, we investigated the post-transcriptional regulation of iron homeostasis. TfR1 (TFRC) and H-ferritin (FTH) mRNAs were quantified in fibroblasts grown in either low (−FAC) or high iron conditions (+FAC) for three days, by digital droplet PCR (ddPCR). TFRC mRNAs levels were similar in control and FRDA fibroblasts grown in low iron condition (−FAC) and decreased in high iron conditions, suggesting a normal down regulation of TFRC transcript (FIG. 2B). Ferritin mRNAs simultaneously increased in control and FRDA fibroblasts grown in high iron condition (FIG. 2C). These results suggest an efficient post-transcriptional regulation of TfR1 and ferritin in FRDA fibroblasts.

Figure 2D:
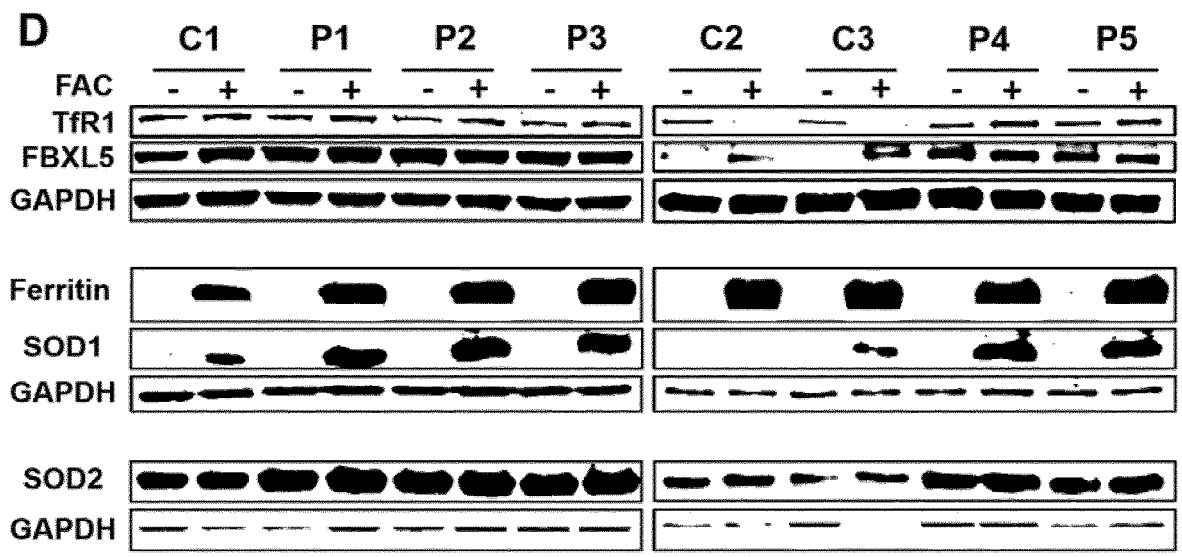

Consistently, western blot analyses detected in control cells grown in high iron condition (+FAC), low levels of TfR1 prevented iron from accumulating and H- and L-ferritin levels were also increased, allowing iron storage (FIG. 2D). Increasing cellular iron induced strong cytosolic and mitochondrial ROS overproduction as shown by high levels SOD1-2. In these conditions (+FAC), FRDA fibroblasts failed to down regulate and even increased TfR1 content, despite high steady-state ferritin levels. Similar results were observed with FBXL5 (FIG. 2D). The combined increase of TfR1 and ferritin in the context of iron overload is paradoxical, as stored iron should down regulate TfR1 levels and metal import. This result suggests that TfR1 apparently escaped IRPs regulation in FRDA fibroblasts. Remembering that post-transcriptional regulation of TfR1 is unaffected, these results suggest an abnormal post-translational regulation of TfR1 in FRDA, as previously described in NBIA (Drecourt et al., 2018).

TfR1 Accumulates at Cell Surface of FRDA Fibroblasts

Figures 3A, 3B:
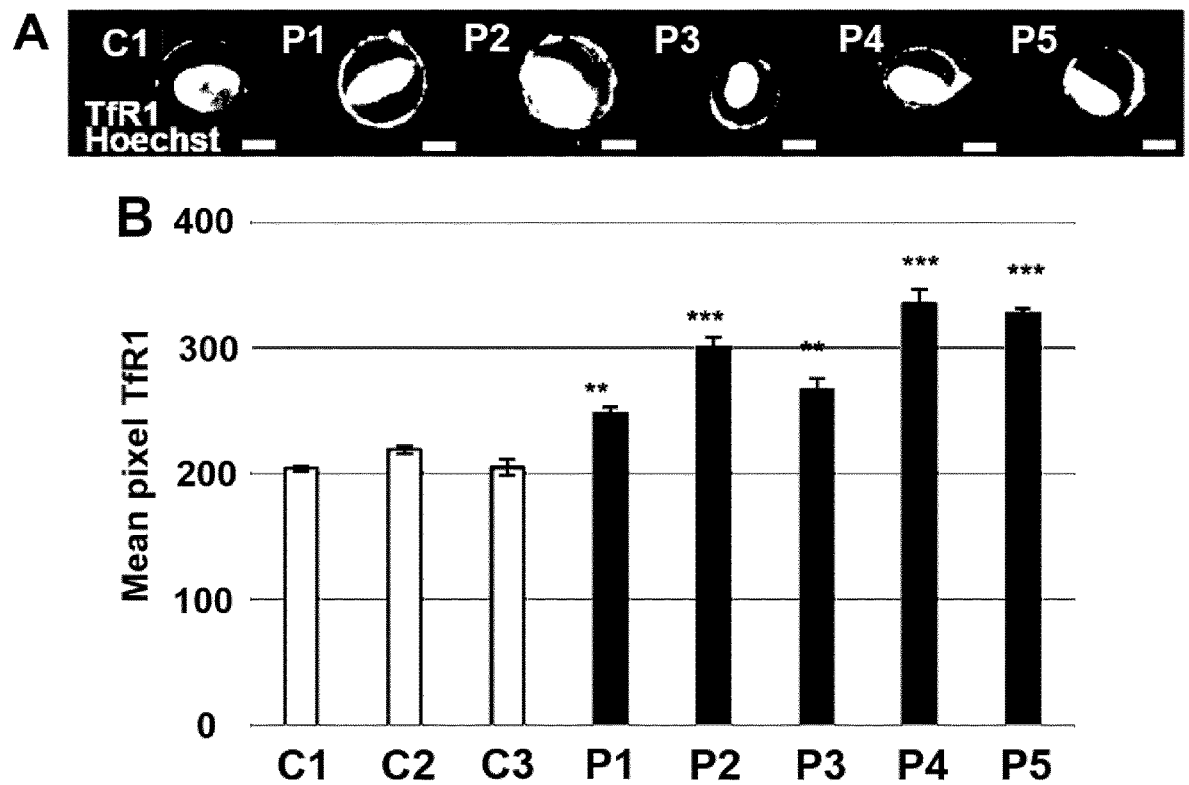

We hypothesized that increased steady-state level of TfR1 could be related to accumulating membrane TfR1 in FRDA, as observed in NBIA. TfR1 amounts were quantified by immunofluorescence using next generation imaging flow cytometry using Amnis Imagestream(X) Mark II which combines flow cytometry with detailed cell-imaging and functional studies. This analysis showed increased amounts of TfR1 at cell surface of FRDA fibroblasts compared to controls (FIG. 3A). Quantification of TfR1 in >20,000 fibroblasts grown in basal conditions using the IDEAS software (Amnis Corporation) revealed a significant increase of TfR1 signal in patients (FIG. 3B). These results indicate that despite iron overload and correct post-transcriptional down-regulation, FRDA fibroblasts accumulate TfR1 at cell membrane, hampering them to regulate iron uptake.

Delayed Transferrin Recycling in FRDA Fibroblasts

Figure 3C:
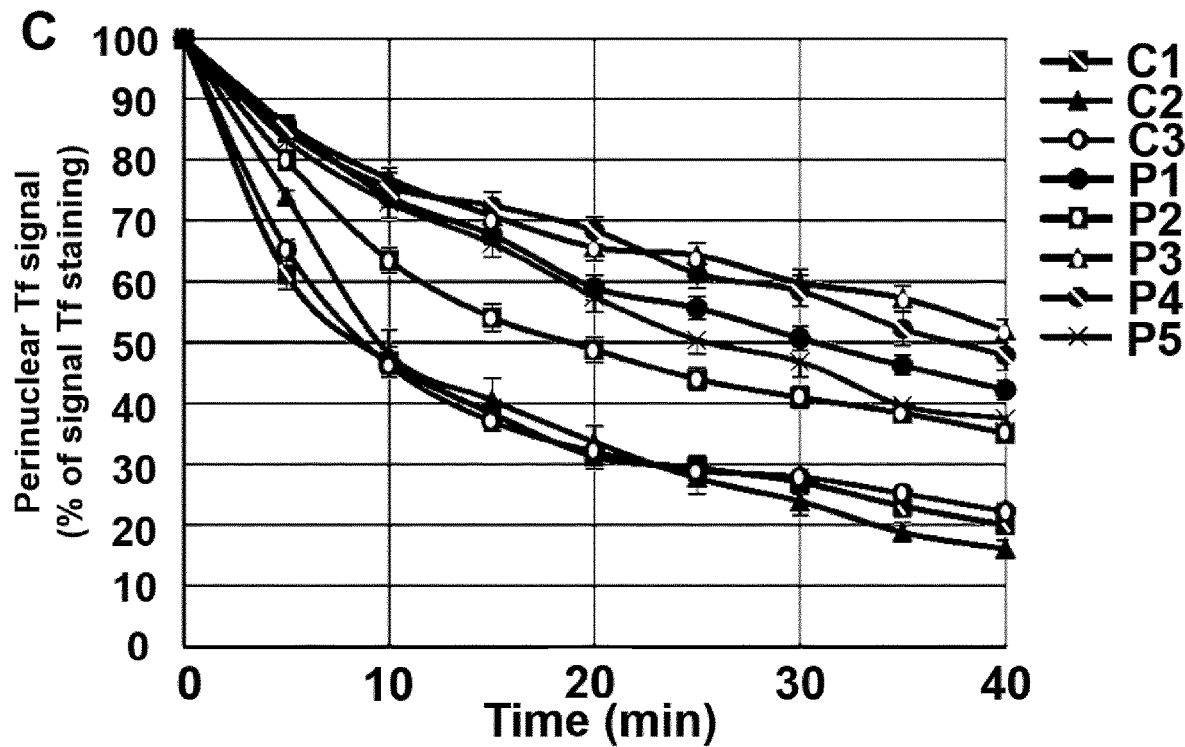

Spinning-disk confocal microscopy was used to assess perinuclear immunofluorescence intensity of transferrin (Tf)-Alexa555 staining in patient and control fibroblasts. At T0 of Tf-Alexa555 pulse and chase, Tf staining was similar in patient and control cells. Control fibroblasts displayed a rapid decrease of Tf staining ascribed to Tf recycling (FIG. 3C). By contrast, Tf recycling was significantly delayed in FRDA fibroblasts as the specific signal aggregated in the vicinity of nucleus, failed to decline after 10 min of Tf-Alexa555 incubation and was still delayed later (FIG. 3C).

TfR1 Palmitoylation in FRDA Fibroblasts

Figure 4A:
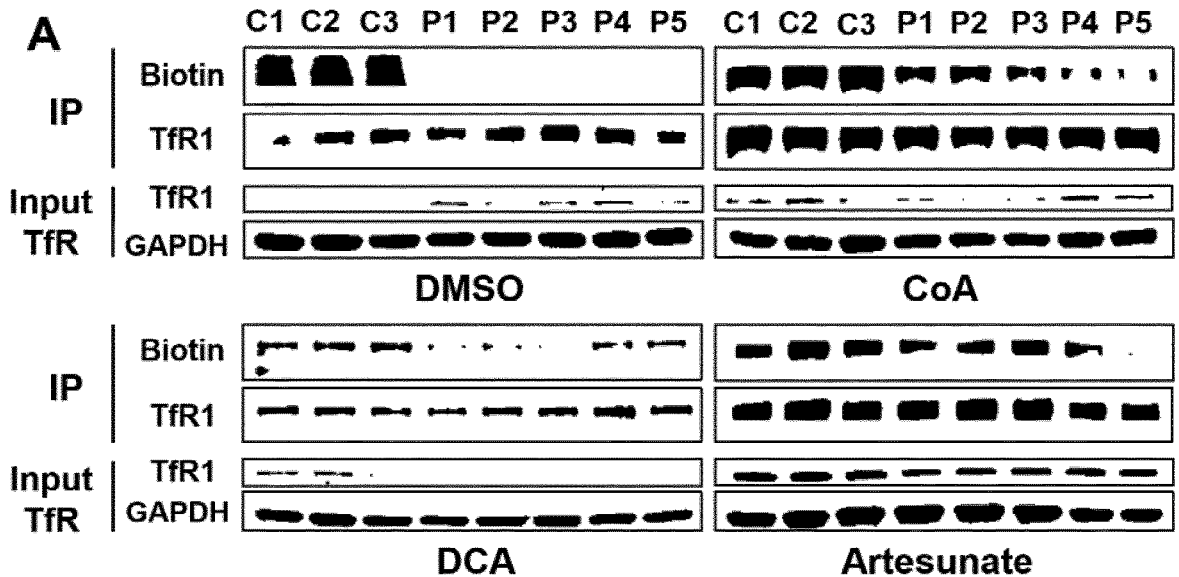
Figures 4B, 4C:
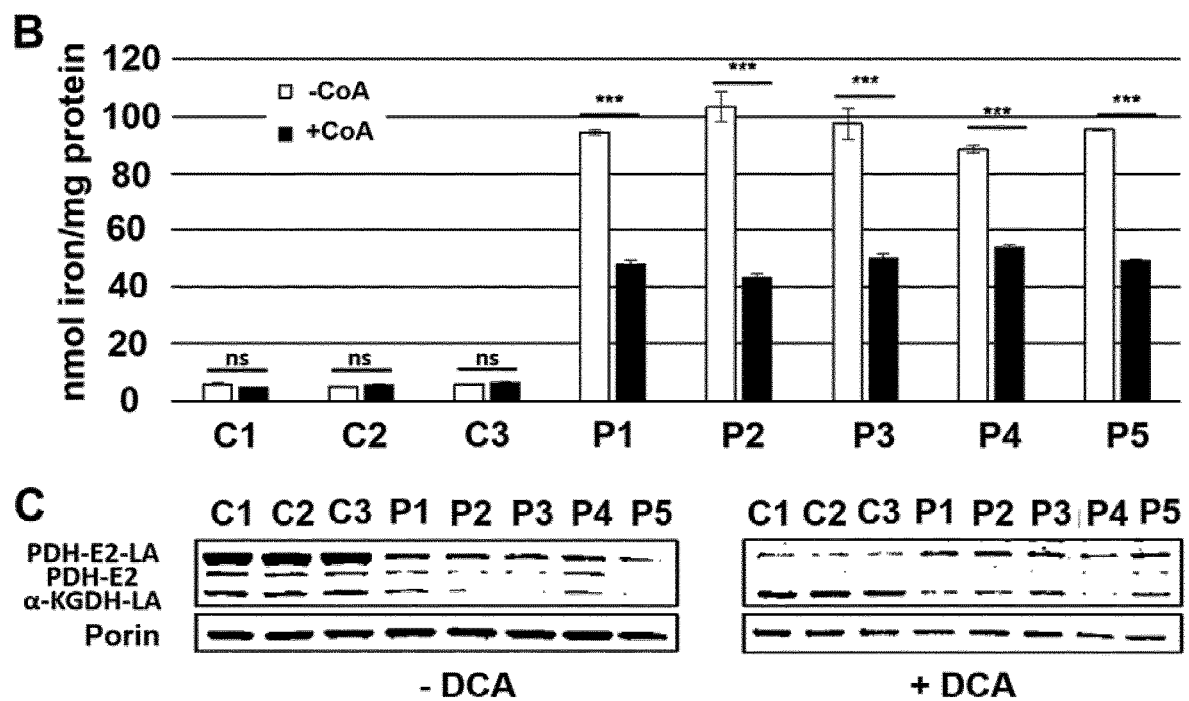

TfR1 is post-translationally modified by covalent attachment of S-acyl radicals to $Cys^{62}$ and $Cys^{67}$ via thioester bonds, palmitate being the predominant fatty acid donor. Decreased palmitoylation has been previously shown to increase TfR1 endocytosis and iron uptake (Alvarez et al., 1990). Moreover, a defective TfR1 palmitoylation has been recently reported in NBIA fibroblasts where iron homeostasis is also altered (Drecourt et al., 2018). Studying cultured cells of FRDA patients revealed a dramatic decrease of TfR1 palmitoylation to only 16-22% of control values, suggesting that frataxin deficiency severely impacts TfR1 palmitoylation for an as yet unknown reason (FIG. 4A). Acetyl-Coenzyme A (CoA) is the sole donor of acetyl groups for palmitoyl transferases. We previously reported that adding CoA to cultured fibroblasts carrying biallelic mutations in two NBIA genes involved in CoA biosynthesis (PANK2 and CRAT) resulted in an increased TfR1 palmitoylation, suggesting that impaired CoA biosynthesis secondarily alters TfR1 palmitoylation (Drecourt et al., 2018). Cells can obtain CoA from extracellular sources, as CoA can be hydrolyzed extracellularly by ectonucleotide pyrophosphatases, thus producing membrane-permeant 4'-phosphopantetheine, intracellularly converted into CoA (Srinivasan et al., 2015). Supplementing cultured cells with CoA 25 µM for 72 h resulted in an increased TfR1 palmitoylation in FRDA fibroblasts (2.1 to 3.2-fold increase, FIG. 4A), suggesting that frataxin deficiency limits the CoA pool, secondarily impacting TfR1 palmitoylation. CoA supplementation also decreased steady state level of TfR1 in FRDA fibroblasts (FIG. 4A). Moreover, at variance with controls, FRDA fibroblasts grown in high iron conditions (+FAC) and supplemented with CoA 25 µM for 72 h showed a 1.6-2.4 fold decrease of cellular iron content (FIG. 4B). This suggests a direct link between frataxin deficiency, CoA availability, TfR1 palmitoylation and iron homeostasis.

Impaired TfR1 Palmitoylation in FRDA Fibroblasts is Related to Defective PDH Lipoylation Lipoic acid synthase (LIAS) is a [4Fes-4S] cluster-containing protein and a key enzyme of lipoic acid (LA) synthesis. LA is a cofactor of several mitochondrial proteins including dihydrolipoamide acetyltransferase (DLAT or PDH-E2), one of the three pyruvate dehydrogenase (PDH) subunits. Cultured fibroblasts of patients carrying biallelic mutations in various genes involved in ISC biogenesis (NFU1, IBA57, ISCA2 and FDX1L) present an impaired lipoylation of DLAT and other mitochondrial proteins and a decreased PDH activity (Lebigot et al., 2017).

Moreover, FXN depletion in mice (Martelli et al., 2015) and knock-down of FXN in HeLa cells resulted in a strongly defective lipoylation of PDH and α-ketoglutarate dehydrogenase (α-KGDH, Tong et al. 2018). We also observed an altered lipoylation of PDH-E2 and α-KGDH and a decreased steady-state level of PDH-E2 subunit in FRDA fibroblasts (FIG. 4C). Considering that CoA supplementation improved TfR1 palmitoylation, we hypothesized that frataxin defect could impact TfR1 palmitoylation via defective PDH lipoylation, especially as acetyl-CoA is mainly produced by oxidative decarboxylation of pyruvate by the PDH complex in mitochondria. Dichloroacetate (DCA), an inhibitor of PDH kinase (PDHK) that inactivates the PDH complex, is known to increase pyruvate oxidation and acetyl-CoA pool. Supplementing FRDA fibroblasts with DCA 5 mM for 72 h significantly increased TfR1 palmitoylation just as did CoA (FIG. 4A), demonstrating that reduced PDH activity indeed affects the CoA pool available for TfR1 palmitoylation. DCA also significantly reduced the steady state level of TfR1 in FRDA fibroblasts (FIG. 4A). Moreover, DCA supplementation completely or partially rescued the steady-state level of PDH-E2 and altered lipoylation of PDH and α-KGDH in FRDA fibroblasts, probably as octanoic acid, the precursor of lipoic acid is synthesized through fatty acid oxidation.

Artesunate Rescues TfR1 Palmitoylation, Tf Recycling and Iron Overload in FRDA Fibroblasts Artesunate is known to alter cellular iron homeostasis by palmitoylation of TfR1 and to reduce membrane TfR1 (Ba et al., 2012). Adding artesunate 25 µM for 48 h to the culture medium enhanced TfR1 palmitoylation to 80% of controls and significantly decreased the steady state level of TfR1 in FRDA fibroblasts (FIG. 4A). Imaging flow cytometry showed that artesunate significantly decreased membrane TfR1 in FRDA fibroblasts (15-30% decrease) while it slightly increased in control cells (1.1 to 1.3-fold, FIGS. 5A and 5B).

Figures 5B, 5C, 5D:
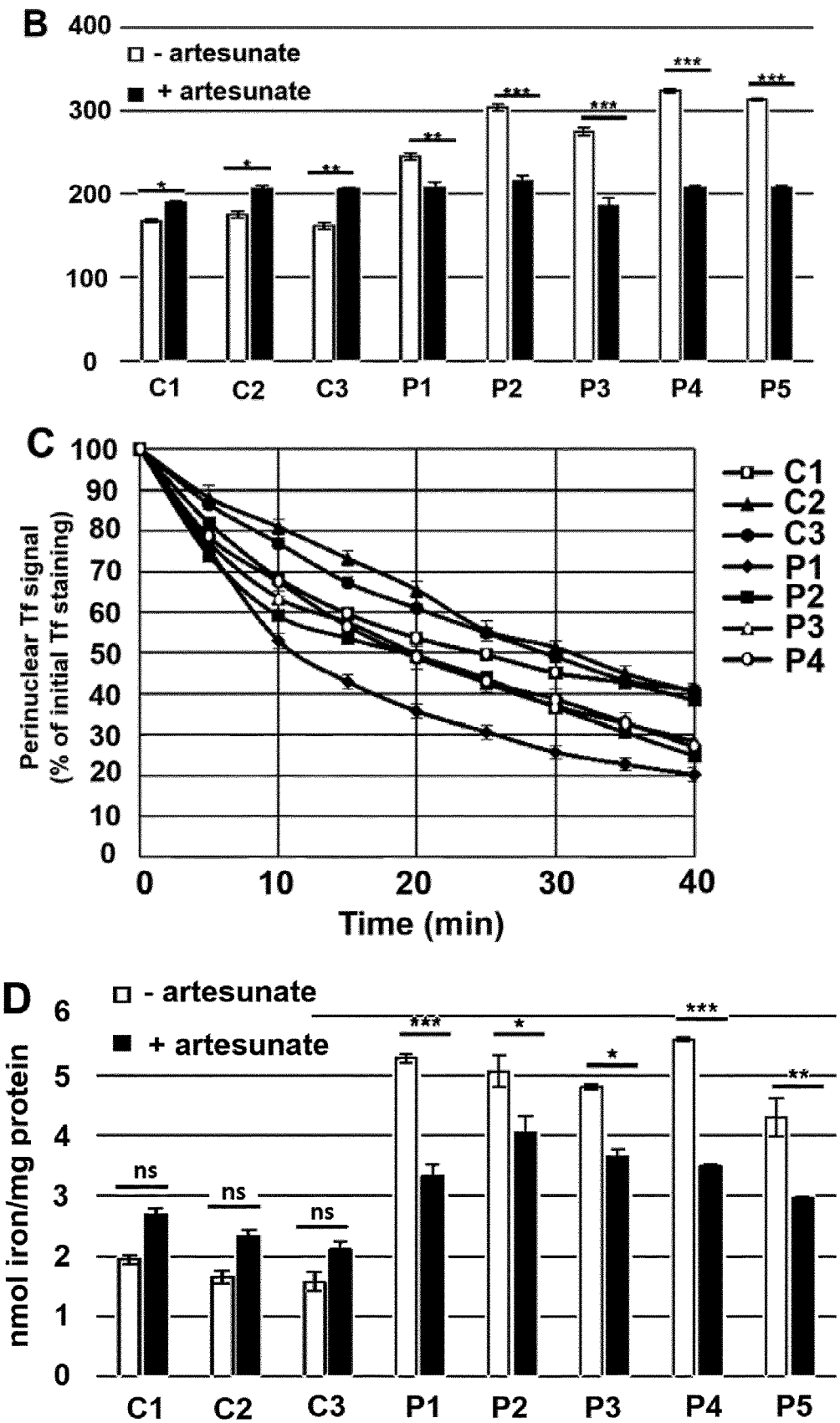
Figures 6A, 6B:
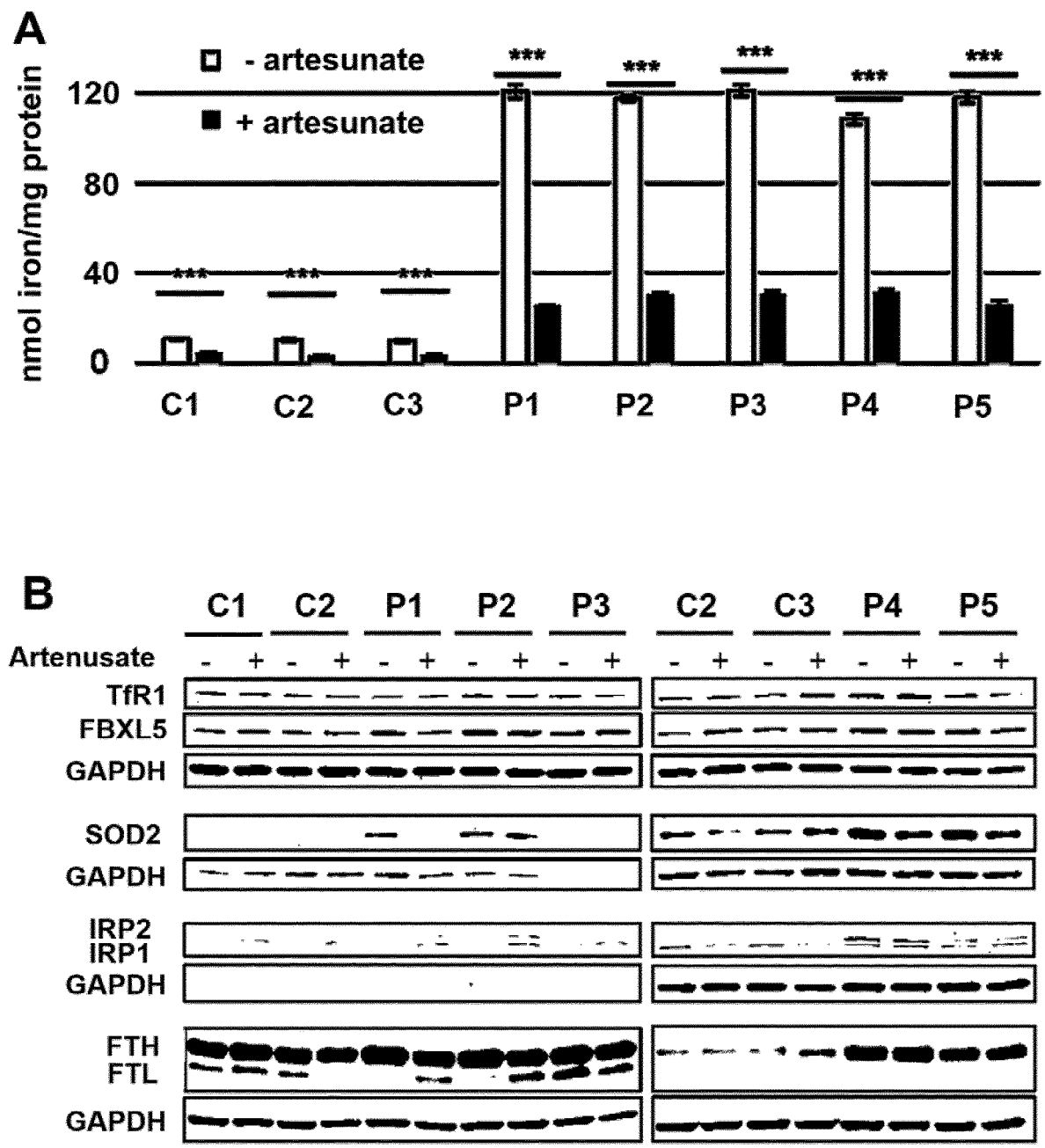

In order to investigate the effect of artesunate on Tf recycling, immunofluorescence intensity of Tf-Alexa555 staining was recorded in FRDA and control cells. Artesunate rapidly reduced Tf signal to control values in FRDA fibroblasts, with a complete rescue of delayed Tf recycling and a disappearance of perinuclear Tf staining. (FIG. 5C). Consistently, iron overload fell to 62-79% of initial cellular iron content after a 48 h artesunate supplementation in FRDA fibroblasts grown in basal conditions (FIG. 5D). It should be noted that control cells treated with artesunate display a slight delay of Tf recycling and a light but non-significant increase of iron content (FIGS. 5C and 5D). Adding 25 µM artesunate to cultured FRDA fibroblasts grown in high iron condition (100 µM FAC) resulted in a 71-79% decrease of cellular iron content, illustrating the spectacular rescue of patient cell ability to regulate iron uptake and handling. (FIG. 6A). Of note, artesunate also decreased iron content of control cells grown in high iron conditions (FIG. 6A).

Western blot analyses confirmed that artesunate supplementation of FRDA fibroblasts decreased TfR1 that reached 136% of control values in artesunate-free medium (FIG. 6B). Moreover, ferritin and FBXL5 steady state levels returned to control values paralleling the decreased iron content that possibly reduced the ROS production as suggested by decreased SOD2. IRP1-2 were not modified by artesunate treatment. In control cells, the slight increase of TfR1 by artesunate treatment could possibly result from the slight but non-significant decrease of TfR1 palmitoylation. Nevertheless, ferritin, FBXL5 were not modified.

Figure 7A:
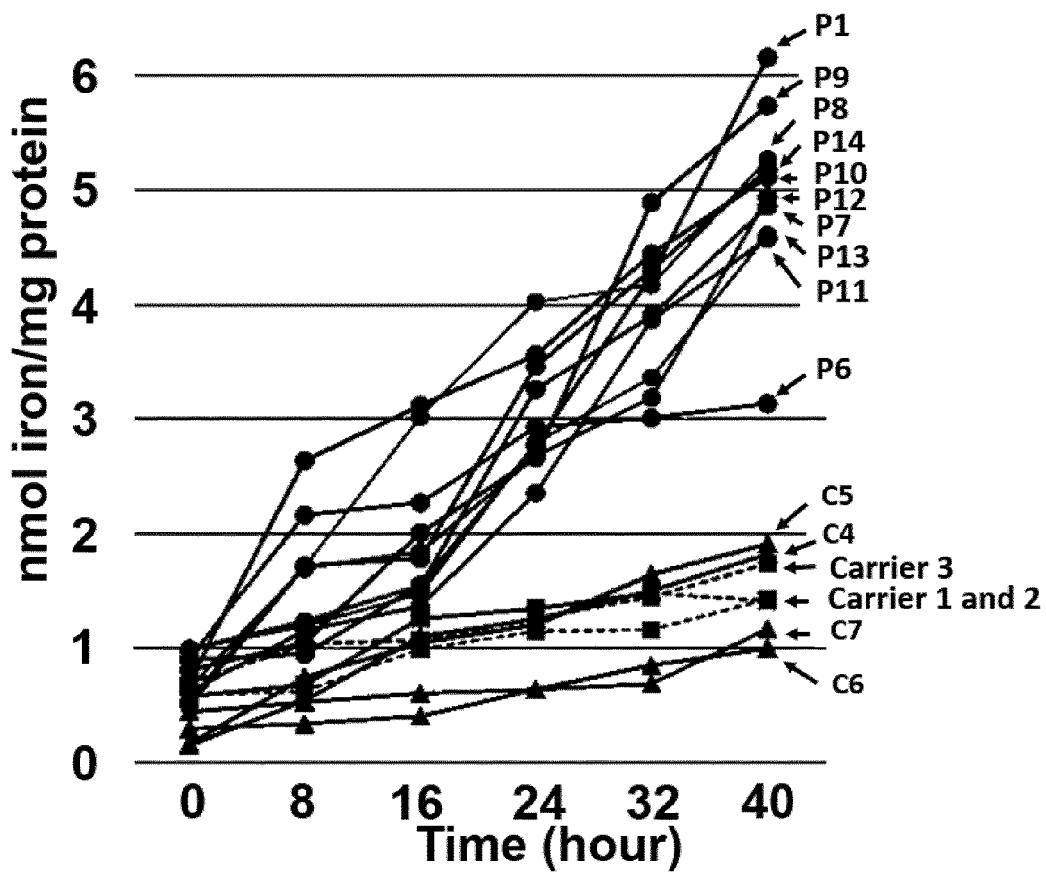
Figure 7B:
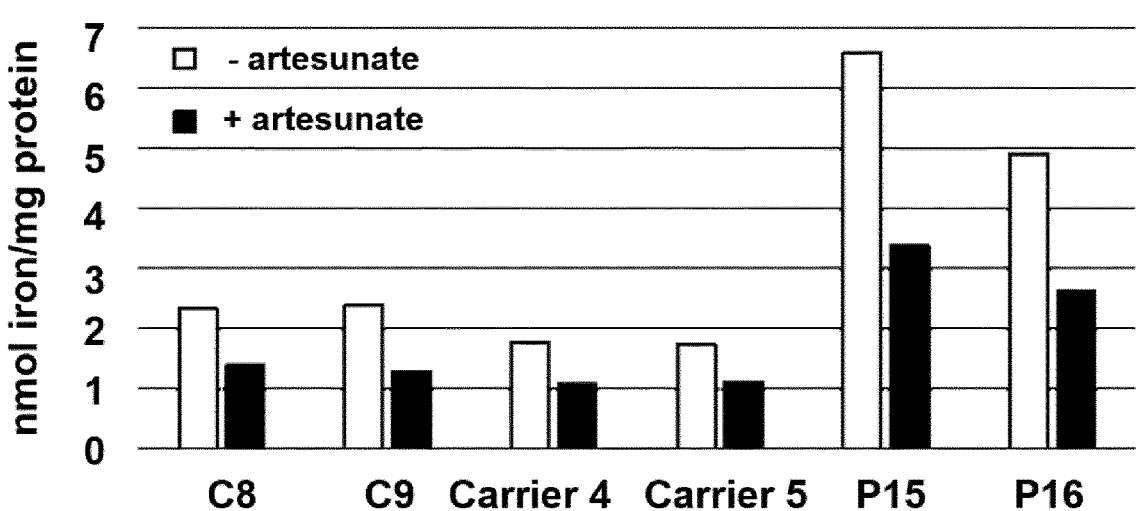

Artesunate Reduces Iron Overload in Peripheral Blood Mononuclear Cells of FRDA Patients Total cellular iron content of peripheral blood mononuclear cells (PBMCs) grown in high iron conditions for 40 h was quantified in patients and controls. After 24 h, PBMC iron content of FRDA patients was much higher than controls and eventually doubled after 40 h (FIG. 7A). This suggested that PBMCs are also unable to regulate iron uptake in high iron conditions. PBMC iron content of three heterozygous carriers was similar to control values, even after a 40 h incubation in high iron medium. Adding artesunate 25 µM to the PBMC culture medium resulted in a two-fold decrease of iron content in both FRDA and control PBMCs (FIG. 7B).

Discussion

Here, we report on disturbed cellular iron homeostasis and defective palmitoylation of transferrin receptor, TfR1, in cultured fibroblasts of FRDA patients. Both cytosolic and mitochondrial compartments were found to abnormally accumulate large amounts of iron. We also observed that lipoylation of the PDH complex was defective, owing to impaired ISC assembly in lipoic acid synthase. Defective lipoylation of the PDH complex dramatically reduced in turn the acetyl-CoA pool and caused a secondary defect of TfR1 palmitoylation. This resulted in an accumulation of membrane TfR1, preventing FRDA fibroblasts from regulating iron uptake and Tf recycling. Finally, we show that artesunate improved TfR1 palmitoylation, decreased membrane TfR1 and rescued Tf recycling and iron overload in FRDA fibroblasts. Similarly, dichloroacetate and CoA also increased TfR1 palmitoylation.

Iron dysregulation in Friedreich ataxia has long been recognized and is commonly thought to feature mitochondrial iron accumulation, with cytosolic iron depletion. Here, we show that iron massively accumulated in cytosol, and to a lesser extent in mitochondria. Increased ferritin and FBXL5 steady-state levels paralleled iron accumulation and elevated SOD1-2 suggested increased ROS production, possibly related to iron overload. Cytosolic iron content has seldom been previously assessed, and to our knowledge, not formally quantified in the various cell and animal models of frataxin deficiency. The alleged cytosolic iron depletion at the expense of mitochondria is mainly based on mitochondrial iron overload (Babcock et al., 1997; Puccio et al., 2001) with no cytosolic quantification, but an increased TfR1 and decreased ferritin steady-state levels related to activation of IRP1 binding to IRE (Martelli et al., 2015; Telot et al., 2018; Whitnall et al., 2012). Surprisingly in our study, we found accumulating iron to be relatively higher in cytosol than in mitochondria. It should be bore in mind that increased levels of ferritin have been found in heart of FRDA patients (Ramirez et al., 2012) and muscle of MCK conditional frataxin knock-out mice (Whitnall et al., 2012), suggesting that iron accumulation is variable among tissues.

Cellular iron homeostasis is mainly regulated by a post-transcriptional mechanism allowing TfR1 mRNA to decrease, thus limiting iron uptake in high iron conditions. This post-transcriptional regulation by IRP/IRE functioned normally in FRDA fibroblasts, as TFRC transcripts were efficiently down-regulated for limiting iron uptake in high iron conditions. Therefore, increased TfR1 steady state levels and membrane TfR1 accumulation in FRDA fibroblasts pointed to another level of regulation, i.e. a post-translational regulation of TfR1, as previously reported in NBIA (Drecourt et al., 2018).

TfR1 is post-translationally modified by S-acylation, particularly palmitoylation, as palmitate (C16:0) is the major lipid donor to S-acylated proteins. Levels of TfR1 palmitoylation are known to control cellular iron, as mutations of $Cys^{62}$ and $Cys^{67}$, the major sites of TfR1 palmitoylation, caused increased TfR1 internalization and iron overload. Here we provide evidence of defective TfR1 palmitoylation in FRDA fibroblasts and subsequent accumulation of membrane and cytosolic TfR1. Because post-translational regulation of TfR1 by palmitoylation rapidly modulates cellular iron content, we hypothesize that this regulatory system is impaired in FRDA and contribute, at least in part, to the disease mechanism. We have previously ascribed defective TfR1 palmitoylation to impaired CoA synthesis related to PANK2 and CRAT mutations in NBIA (Drecourt et al., 2018). While PANK2 and CRAT are directly involved in CoA synthesis, increased TfR1 palmitoylation and decreased iron content following CoA supplementation of cultured FRDA fibroblasts strongly suggests that frataxin deficiency induces a secondary reduction of the CoA/acetyl-CoA pool. As other defects of ISC biogenesis machinery, frataxin deficiency impacts a variety of cellular proteins including mitochondrial LIAS, resulting in a decreased lipoylation of at least DLAT subunit of PDH and αKGDH (Lebigot et al., 2017; Martelli et al., 2015; Tong et al., 2018). Acetyl-CoA is predominantly generated in the mitochondria by decarboxylation of pyruvate, and the CoA pool is expected to be decreased in FRDA fibroblasts owing to defective DLAT lipoylation. Increased TfR1 palmitoylation following inhibition of PDH kinase by DCA supports this hypothesis.

FRDA fibroblasts also displayed a defective endosome circuitry, illustrated by delayed Tf recycling. Owing to impaired endosome recycling, we hypothesize that iron overload may not only result from increased amounts of membrane TfR1 but also from the impaired release of cytosolic iron, stored in uncoated vesicles. Palmitoylation is known to increase protein lipophilicity and to regulate their trafficking, stability and subcellular distribution. As a number of endosome recycling proteins are palmitoylated, it is possible that altered palmitoylation of other, as yet undetermined, endosomal proteins may also alter TfR1 recycling and contribute to iron overload.

Identifying abnormal palmitoylation of TfR1 in FRDA fibroblasts adds an additional level of complexity to the pathophysiology of the disease. On the other hand, it helps understanding the variable clinical consequences of frataxin deficiency as the time course and/or tissue specific expression of ISC-containing proteins may actually control organ involvement and explains why respiratory chain deficiency is found in heart and not in muscle or fibroblasts of FRDA patients (Rotig et al., 1997). Various tissue requirements for acetyl-CoA or SIRT3 inhibition (Wagner et al., 2012) known to influence cellular iron content (Jeong et al., 2015) may also contribute to the tissue-specific expression of FRDA. In support of this, respiratory chain deficiency was observed in heart of frataxin-deficient mice aged 7 weeks while iron overload appeared only 3 weeks later (Puccio et al., 2001).

Other consequences of frataxin deficiency may also contribute to secondarily reduce the mitochondrial acetyl-CoA pool. As shown for ISCU defects (Tong et al., 2018), tissues with reduced mitochondrial aconitase activity accumulate citrate, which activates acetyl-CoA carboxylase and therefore lowers the acetyl CoA pool by inducing malonyl-CoA formation. Inhibition of SIRT3 deacetylase reported in mouse induces hyperacetylation of several mitochondrial proteins known to reduce their activities (Wagner et al., 2012). Hyperacetylation of one of the main targets of SIRT3, mitochondrial acetyl-CoA synthetase 2, may reduce acetyl-CoA synthesis. Along the same lines, iron accumulation may increase synthesis of sphingolipids and palmitoyl-CoA and acyl-CoA consumption, lowering in turn the palmitoyl-CoA and acyl-CoA pool required for TfR1 palmitoylation (Chen et al., 2016a). Indeed, depletion of frataxin reduces overall histone acetylation (Tong et al., 2018) as is also the case in impaired CoA biosynthesis related to PANK2 mutations (Siudeja et al., 2011).

Finally, we also show that artesunate, CoA and DCA significantly induced TfR1 palmitoylation, reduced TfR1 steady-state level and membrane TfR1 accumulation. Artesunate rescued Tf recycling and restored the ability of FRDA fibroblasts to regulate iron uptake. Artesunate has potent anticancer properties because it induces iron depletion, that is toxic for cancer cells (Lai et al., 2013). It is also used to treat malaria caused by *Plasmodium falciparum*. Although its safety profile and pharmacokinetics have not been assessed in neurodegenerative diseases, several millions of subjects have received artemisinin with very few side effects (Efferth and Kaina, 2010). Our data suggest that consideration should be given to this compound and other drugs increasing TfR1 palmitoylation, as possible therapeutic approaches in FRDA especially as iron mediated toxicity has been shown to contribute to neurodegeneration in *Drosophila* model of FRDA (Chen et al., 2016b). Because PBMCs of FRDA patients were unable to regulate iron uptake in high iron conditions, as observed in FRDA-iPSC cardiomyocytes (Lee et al., 2014), we believe that monitoring iron homeostasis and TfR1 immunofluorescence in vivo could be regarded as useful, early endpoints to monitor future clinical trials in FRDA patients

REFERENCES

Throughout this application, various references describe the state of the art to which this invention pertains. The disclosures of these references are hereby incorporated by reference into the present disclosure.

Alvarez, E., Girones, N., and Davis, R. J. (1990). Inhibition of the receptor-mediated endocytosis of diferric transferrin is associated with the covalent modification of the transferrin receptor with palmitic acid. J Biol Chem 265, 16644-16655.

Ba, Q., Zhou, N., Duan, J., Chen, T., Hao, M., Yang, X., Li, J., Yin, J., Chu, R., and Wang, H. (2012). Dihydroartemisinin exerts its anticancer activity through depleting cellular iron via transferrin receptor-1. PLoS One 7, e42703.

Babcock, M., de Silva, D., Oaks, R., Davis-Kaplan, S., Jiralerspong, S., Montermini, L., Pandolfo, M., and Kaplan, J. (1997). Regulation of mitochondrial iron accumulation by Yfh1p, a putative homolog of frataxin. Science 276, 1709-1712.

Barbeito, A. G., Levade, T., Delisle, M. B., Ghetti, B., and Vidal, R. (2010). Abnormal iron metabolism in fibroblasts from a patient with the neurodegenerative disease hereditary ferritinopathy. Molecular neurodegeneration 5, 50.

Chen, K., Ho, T. S., Lin, G., Tan, K. L., Rasband, M. N., and Bellen, H. J. (2016a). Loss of Frataxin activates the iron/sphingolipid/PDK1/Mef2 pathway in mammals. Elife 5.

Chen, K., Lin, G., Haelterman, N. A., Ho, T. S., Li, T., Li, Z., Duraine, L., Graham, B. H., Jaiswal, M., Yamamoto, S., et al. (2016b). Loss of Frataxin induces iron toxicity, sphingolipid synthesis, and Pdk1/Mef2 activation, leading to neurodegeneration. Elife 5.

Drecourt, A., Babdor, J., Dussiot, M., Petit, F., Goudin, N., Garfa-Traore, M., Habarou, F., Bole-Feysot, C., Nitschke, P., Ottolenghi, C., et al. (2018). Impaired Transferrin Receptor Palmitoylation and Recycling in Neurodegeneration with Brain Iron Accumulation. Am J Hum Genet 102, 266-277.

Efferth, T., and Kaina, B. (2010). Toxicity of the antimalarial artemisinin and its dervatives. Crit Rev Toxicol 40, 405-421.

Jeong, S. M., Lee, J., Finley, L. W., Schmidt, P. J., Fleming, M. D., and Haigis, M. C. (2015). SIRT3 regulates cellular iron metabolism and cancer growth by repressing iron regulatory protein 1. Oncogene 34, 2115-2124.

Lai, H. C., Singh, N. P., and Sasaki, T. (2013). Development of artemisinin compounds for cancer treatment. Invest New Drugs 31, 230-246.

Lebigot, E., Gaignard, P., Dorboz, I., Slama, A., Rio, M., de Lonlay, P., Heron, B., Sabourdy, F., Boespflug-Tanguy, O., Cardoso, A., et al. (2017). Impact of mutations within the [Fe—S] cluster or the lipoic acid biosynthesis pathways on mitochondrial protein expression profiles in fibroblasts from patients. Mol Genet Metab.

Lee, Y. K., Ho, P. W., Schick, R., Lau, Y. M., Lai, W. H., Zhou, T., Li, Y., Ng, K. M., Ho, S. L., Esteban, M. A., et al. (2014). Modeling of Friedreich ataxia-related iron overloading cardiomyopathy using patient-specific-induced pluripotent stem cells. Pflugers Arch 466, 1831-1844.

Martelli, A., and Puccio, H. (2014). Dysregulation of cellular iron metabolism in Friedreich ataxia: from primary iron-sulfur cluster deficit to mitochondrial iron accumulation. Frontiers in pharmacology 5, 130.

Martelli, A., Schmucker, S., Reutenauer, L., Mathieu, J. R., Peyssonnaux, C., Karim, Z., Puy, H., Galy, B., Hentze, M. W., and Puccio, H. (2015). Iron regulatory protein 1 sustains mitochondrial iron loading and function in frataxin deficiency. Cell Metab 21, 311-322.

Metodiev, M. D., Lesko, N., Park, C. B., Camara, Y., Shi, Y., Wibom, R., Hultenby, K., Gustafsson, C. M., and Larsson, N. G. (2009). Methylation of 12S rRNA is necessary for in vivo stability of the small subunit of the mammalian mitochondrial ribosome. Cell Metab 9, 386-397.

Moura, I. C., Lepelletier, Y., Arnulf, B., England, P., Baude, C., Beaumont, C., Bazarbachi, A., Benhamou, M., Monteiro, R. C., and Hermine, O. (2004). A neutralizing monoclonal antibody (mAb A24) directed against the transferrin receptor induces apoptosis of tumor T lymphocytes from ATL patients. Blood 103, 1838-1845.

Muhlenhoff, U., Hoffmann, B., Richter, N., Rietzschel, N., Spantgar, F., Stehling, O., Uzarska, M. A., and Lill, R. (2015). Compartmentalization of iron between mitochondria and the cytosol and its regulation. Eur J Cell Biol 94, 292-308.

Mukhopadhyay, P., Rajesh, M., Hasko, G., Hawkins, B. J., Madesh, M., and Pacher, P. (2007). Simultaneous detection of apoptosis and mitochondrial superoxide production in live cells by flow cytometry and confocal microscopy. Nature protocols 2, 2295-2301.

Puccio, H., Simon, D., Cossee, M., Criqui-Filipe, P., Tiziano, F., Melki, J., Hindelang, C., Matyas, R., Rustin, P., and Koenig, M. (2001). Mouse models for Friedreich ataxia exhibit cardiomyopathy, sensory nerve defect and Fe—S enzyme deficiency followed by intramitochondrial iron deposits. Nat Genet 27, 181-186.

Ramirez, R. L., Qian, J., Santambrogio, P., Levi, S., and Koeppen, A. H. (2012). Relation of cytosolic iron excess to cardiomyopathy of Friedreich's ataxia. Am J Cardiol 110, 1820-1827.

Rotig, A., de Lonlay, P., Chretien, D., Foury, F., Koenig, M., Sidi, D., Munnich, A., and Rustin, P. (1997). Aconitase and mitochondrial iron-sulphur protein deficiency in Friedreich ataxia. Nat Genet 17, 215-217.

Siudeja, K., Srinivasan, B., Xu, L., Rana, A., de Jong, J., Nollen, E. A., Jackowski, S., Sanford, L., Hayflick, S., and Sibon, O. C. (2011). Impaired Coenzyme A metabolism affects histone and tubulin acetylation in Drosophila and human cell models of pantothenate kinase associated neurodegeneration. EMBO molecular medicine 3, 755-766.

Srinivasan, B., Baratashvili, M., van der Zwaag, M., Kanon, B., Colombelli, C., Lambrechts, R. A., Schaap, O., Nollen, E. A., Podgorsek, A., Kosec, G., et al. (2015). Extracellular 4'-phosphopantetheine is a source for intracellular coenzyme A synthesis. Nat Chem Biol 11, 784-792.

Telot, L., Rousseau, E., Lesuisse, E., Garcia, C., Morlet, B., Leger, T., Camadro, J. M., and Serre, V. (2018). Quantitative proteomics in Friedreich's ataxia B-lymphocytes: A valuable approach to decipher the biochemical events responsible for pathogenesis. Biochim Biophys Acta 1864, 997-1009.

Tong, W. H., Maio, N., Zhang, D. L., Palmieri, E. M., Ollivierre, H., Ghosh, M. C., McVicar, D. W., and Rouault, T. A. (2018). TLR-activated repression of Fe—S cluster biogenesis drives a metabolic shift and alters histone and tubulin acetylation. Blood Adv 2, 1146-1156.

Vaubel, R. A., and Isaya, G. (2013). Iron-sulfur cluster synthesis, iron homeostasis and oxidative stress in Friedreich ataxia. Molecular and cellular neurosciences 55, 50-61.

Wagner, G. R., Pride, P. M., Babbey, C. M., and Payne, R. M. (2012). Friedreich's ataxia reveals a mechanism for coordinate regulation of oxidative metabolism via feedback inhibition of the SIRT3 deacetylase. Hum Mol Genet 21, 2688-2697.

Whitnall, M., Suryo Rahmanto, Y., Huang, M. L., Saletta, F., Lok, H. C., Gutierrez, L., Lazaro, F. J., Fleming, A. J., St Pierre, T. G., Mikhael, M. R., et al. (2012). Identification of nonferritin mitochondrial iron deposits in a mouse model of Friedreich ataxia. Proc Natl Acad Sci USA 109, 20590-20595.

The invention claimed is:

1. A method of treating Friedreich ataxia (FRDA) in a patient in need thereof comprising administering to the patient a therapeutically effective amount of a drug that increases TfR1 palmitoylation, wherein the drug that increases TfR1 palmitoylation is the sole active agent.

2. The method of claim 1 wherein the drug is selected from the group consisting of artesunate, dichloroacetate and Coenzyme-A.

3. A method of treating a subject in need thereof with a drug that increases TfR1 palmitoylation, comprising the steps of
   i) measuring the total cellular iron content of peripheral blood mononuclear cells (PBMCs) obtained from the subject and cultured in a medium comprising an amount of iron,
   ii) comparing the total cellular iron content measured in PBMCs from the subject with a predetermined reference value,
   iii) treating the subject with the drug when the total cellular iron content is higher that the differs from a predetermined reference value.

4. The method of claim 3 wherein the drug is selected from the group consisting of artesunate, dichloroacetate and Coenzyme-A.

5. The method of claim 3, wherein the PBMCs are cultured for 0, 8, 16, 24, 32, or 40 h before measuring the total iron content.

6. The method of claim 3 wherein the predetermined reference value is the total cellular iron content of PBMCs obtained from the patient before the treatment.

7. The method of claim 6 wherein when the total cellular iron content is lower than said predetermined reference value, it is concluded that the patient will achieve a response with the drug.

8. The method of claim 3 wherein the predetermined reference value is the total cellular iron content of PBMCs obtained from the patient before the treatment and cultured in the presence of the drug.

9. The method of claim 8 wherein when the total cellular iron content is higher than the predetermined reference value, it is concluded that the patient will not achieve response with the drug; and when the total cellular content iron is the same or lower than the predetermined reference value, it is concluded that the patient will achieve a response with the drug.

10. The method of claim 7, wherein when the total cellular iron content is 0.5; 1; 2; 3; 4; 5; 6; 7; 8; 9; or 10-fold lower than the predetermined reference value, it is concluded that the patient will achieve a response with the drug.

11. The method of claim 9, wherein when the total cellular iron content is 0.5; 1; 2; 3; 4; 5; 6; 7; 8; 9; or 10-fold higher than the predetermined reference value, it is concluded that the patient will not achieve a response with the drug.

12. A method of treating Friedreich ataxia (FRDA) in a patient in need thereof, comprising administering to the patient a therapeutically effective amount of a drug that increases TfR1 palmitoylation, wherein the drug that increases TfR1 palmitoylation is the sole active agent, and wherein the drug that increases TfR1 palmitoylation is selected from the group consisting of artesunate, dichloroacetate and Coenzyme-A.

* * * * *